(12) United States Patent
Shariat (10) Patent No.: US 7,759,077 B2
(45) Date of Patent: Jul. 20, 2010

(54) SOLUBLE FAS URINARY MARKER FOR THE DETECTION OF BLADDER TRANSITIONAL CELL CARCINOMA

(76) Inventor: Shahrokh F. Shariat, 3922 Gilbert Ave., #203, Dallas, TX (US) 75219

(*) Notice: Subject to any disclaimer, the term of this patent is extended or adjusted under 35 U.S.C. 154(b) by 0 days.

(21) Appl. No.: 11/497,779

(22) Filed: Aug. 2, 2006

(65) Prior Publication Data
US 2007/0031905 A1 Feb. 8, 2007

Related U.S. Application Data

(60) Provisional application No. 60/704,800, filed on Aug. 2, 2005.

(51) Int. Cl.
*G01N 33/574* (2006.01)
(52) U.S. Cl. ......................... 435/7.23; 435/7.1
(58) Field of Classification Search ................. None
See application file for complete search history.

(56) References Cited

U.S. PATENT DOCUMENTS 6,846,637 B1 1/2005 Chiodi

OTHER PUBLICATIONS

Svatek, R.S., Herman, M.P., Lotan, Y., Casella, R., Hsieh, J., Sagalowsky, A.I., and Shariat, S.F. Soluble Fas—a promising novel urinary marker for the detection of recurrent superficial bladder cancer. Cancer, 2006. vol. 1206, pp. 1701-1707.*
Perabo, F.G.E., Mattes, R.H., Wirger, A., Steiner, G., Kamp, S., Schmidt, D., Pegelow, K., Von Ruecker, A., and Muller, S.C. Soluble Fas and Fas-ligand in bladder cancer in vitro and in vivo. Urologic Oncology, 2001. vol. 6, pp. 163-169.*
Mizutani, Y., Yoshida, O., and Bonavida, B. Prognostic significance of soluble Fas in the serum of patients with bladder cancer. Journal of Urology, 1998. vol. 160 No. 2, pp. 571-576.*
Senga, Y., Kimura, G., Hattori, T., and Yoshida, K. Clinical evaluation of soluble cytokeratin 19 fragments (CYFRA 21-1) in serum and urine of patients with bladder cancer. Urology, 1996. vol. 48, pp. 703-710.*
Shi, B.B., Goya, N., Okuda, H., Ryoji, O., Nakazawa, H., and Toma, H. Detection and quantification of soluble intercellular adhesion molecule-1 (sICAM-1) in the serum and urine of patients with bladder cancer. International Journal of Urology, 1998. vol. 5 No. 4, pp. 324-328.*
Tockman et al, Cancer Res., 1992, 52:2711s-2718s.*
Arase, H., et al., "Fas-mediated cytotoxicity by freshly isolated natural killer cells." J Exp Med, (1995), 181:1235.
Chopin, D., et al., "Human urinary bladder transitional cell carcinomas acquire the functional Fas ligand during tumor progression." Am J Pathol, (2003), 162:1139.
Delong, E. R., et al., "Comparing the areas under two or more correlated receiver operating characteristic curves: a nonparametric approach." Biometrics, (1988), 44: 837.
Kagi, D., et al., Fas and perforin pathways as major mechanisms of T cell-mediated cytotoxicity. Science, (1994), 265:528.
Lee, S. H., et al., "Transitional cell carcinoma expresses high levels of Fas ligand in vivo." BJU Int, (1999), 83:698.
Lotan, Y., et al., "Sensitivity and specificity of commonly available bladder tumor markers versus cytology: results of a comprehensive literature review and meta-analyses." Urology, (2003), 61:109.
Liu, C., et al., "Differential expression of human Fas mRNA species upon peripheral blood mononuclear cell activation." Biochem J, (1995), 310(3):957.
Millan-Rodriguez, F., et al., "Primary superficial bladder cancer risk groups according to progression, mortality and recurrence." J Urol, (2000), 164:680.
Mizutani, Y., et al., Significance of serum soluble Fas ligand in patients with bladder carcinoma. Cancer, (2001), 92:287.
Mizutani, Y., et al., "Prognostic significance of a combination of soluble Fas and soluble Fas ligand in the serum of patients with Ta bladder cancer." Cancer Biother Radiopharm, (2002), 17:563.
O'Connell, J., et al., "Immune privilege or inflammation? Insights into the Fas ligand enigma." Nat Med, (2001), 7:271.
Pawelec, G.: Immunotherapy and immunoselection—tumour escape as the final hurdle. FEBS Lett, (2004), 567:63.

* cited by examiner

*Primary Examiner*—Misook Yu
*Assistant Examiner*—Mark Halvorson
(74) *Attorney, Agent, or Firm*—Chainey P. Singleton; Edwin S. Flores; Chalker Flores, LLP (57) ABSTRACT

The present invention is an apparatus, system and method for detecting bladder cancer are provided that includes a substrate including one or more sFas binding agents and one or more reagents that indicate the amount of sFas present in the sample.

16 Claims, 3 Drawing Sheets

SOLUBLE FAS URINARY MARKER FOR THE DETECTION OF BLADDER TRANSITIONAL CELL CARCINOMA

CROSS-REFERENCE TO RELATED APPLICATIONS

This application claims priority to U.S. Provisional Application Ser. No. 60/704,800, filed Aug. 2, 2005, the contents of which is incorporated by reference herein in its entirety.

TECHNICAL FIELD OF THE INVENTION

The present invention relates in general to the field of the detection of cancer, and more particularly, to the detection of soluble Fas in the urine to evaluate cancer progression.

BACKGROUND OF THE INVENTION

Without limiting the scope of the invention, its background is described in connection with carcinoma of the genito-urinary tract, as an example. Bladder carcinoma is one of the most common forms of cancer of the genito-urinary tract accounting for 51,000 new cases and 11,000 deaths each year. Bladder cancer is the fourth most common cancer in men and the eighth most common in women, with transitional cell carcinoma (TCC) of the bladder is the most common urothelial malignancy of the urinary tract accounting for about 90% of all bladder tumors. Seventy percent of patients with an initial diagnosis of transitional cell carcinoma have superficial tumors, which can be treated by transurethral resection alone.

The difficulty in detecting and treating bladder cancer makes it a serious concern. Generally, bladder carcinomas are heterogeneous in their ability to progress, e.g., transitional cell carcinomas. TCCs are classified by Grade and depth of invasion (e.g., stage). For example, some TCCs are considered low-grade (e.g., G1 tumors) mostly confined to the mucosa (stage Ta) and behave in a benign fashion, whereas others are intermediately-grade (e.g., G2 tumors) which are moderately aggressive and range from being non-invasive (stage Ta) to invasive (stages T1-T4) with highly aggressive lymphatic and vascular invasion and local and distant metastases, e.g., G3 tumors and carcinoma in situ (CIS).

The high-grade tumors (e.g., bladder tumors) often metastasize rapidly and the invasive disease may already exist at the time of clinical presentation (e.g., hematuria, irritative voiding symptoms etc.). For example, half of the patients develop distant metastasis within two years of diagnosis despite surgery and 60% of them die within 5 years. Additionally, tumor recurrence is a characteristic of bladder carcinoma. As a result of the malignant nature of TCCs, it is critical for detection prior to muscle invasion.

Detecting tumor recurrence in patients with transitional cell carcinoma of the bladder requires close surveillance. Presently, cystoscopy, bladder washings and biopsies are common method to detect and monitor bladder cancer. Many of these procedures are invasive and lack the necessary specificity to adequately diagnose bladder cancer. Urine cytology is a common non-invasive procedure for the diagnosis of bladder cancer; however, it can miss up to 50% of tumors. For example, urine cytology has a low specificity due to its subjective nature. Other detection method may have a high sensitivity, but have a low specificity and detect (e.g., false positive) benign genito-urinary conditions (e.g., kidney stones, benign prostatic hyperplasia etc). Another form of diagnosis is cystoscopy, which allows visualization and direct biopsies of suspicious bladder lesions in the mucosa; however, cystoscopy is invasive and expensive procedure, which cannot be used as a general screening tool for the detection of bladder cancer. For example, other detection methods include tests that detect bladder tumor antigens, e.g. NMP-22. Generally, these tests detect altered expression of proteins or enzyme activity that can be associated with malignancy, or genetic alterations in urinary cells and bladder washings. These procedures often use fluorescence in situ hybridization (FISH) and microsatellite analysis, which is time consuming and costly, as large numbers of cells must be analyzed to obtain an accurate analysis.

Apoptosis is indispensable for normal development, homeostasis of multicellular organisms and defense in that it is the process responsible for cellular destruction and elimination of mutated (e.g., tumors), damaged, or virally infected cells through induction of apoptosis. In many physiologic processes the primary mediator of apoptosis (e.g., tumor cell death) is the cytotoxic T-cells and natural killer cells which also maintenance of immune privileged sites such as the eye, testis, brain, and maternal-fetal interface. A transmembrane cell-surface protein termed Fas regulates apoptotic or programmed cell death through the intercellular interactions of Fas with ligands or effectors. Generally, the interaction between Fas and Fas ligand (FasL) induces apoptosis in cells through activation of the intracellular Fas-associated domain. Natural killer cells and cytotoxic T-cells express the Fas receptor, which engages the Fas-FasL interaction and induce apoptosis of cancer cells through proteolysis and degradation of chromosomal DNA. The Fas signaling pathway consists of a 48 kDa cell surface glycoprotein protein termed Fas protein (also designated CD95L, APO-1). Fas and FasL belong to the TNF (Tumor Necrosis Factor) family, which include CD 40, nerve growth factor receptors and tumor necrosis factor receptors. Specifically, Fas is a member of the of the transmembrane receptor family, while FasL is member of the membrane-associated cytokine family.

Fas plays a role in several pathophysiological conditions including cancer. Fas mRNA and Fas protein expression is altered in certain carcinomas when compared with the corresponding normal tissue expression, which in turn alters cytotoxic T-cells and natural killer cells via the expression of the Fas receptor that engages the Fas-FasL interaction to induce apoptosis of cancer cells. Dysregulation of Fas-mediated apoptosis is thought to play a role in the development and progression of various tumors, e.g., alternative splicing of Fas mRNA can generate soluble forms of Fas that have a deletion or disruption of the membrane-spanning domain. Additionally, FAS mRNA and protein expression increased substantially from normal to prostatic intraepithelial neoplasia, to low grade, to high grade, and to androgen-independent bone metastases. Prior to the present invention, the correlation between components of the FAS system in the urine affect the proliferation of human endothelial cells.

The foregoing problems have been recognized for many years and while numerous solutions have been proposed, none of them adequately address all of the problems in a single device, e.g., high specificity, invasiveness, reproducibility, and reliability.

SUMMARY OF THE INVENTION

As such, there is a need for non-invasive methods to detect bladder cancer by measuring the levels of certain molecular determinants of bladder cancer specifically present in the biological samples (e.g., urine specimens, tissue samples, blood) of patients, while providing specific identification at high sensitivity. More particularly, the methods of the invention are based on the discovery that sFas is produced and excreted by bladder cancer cells and the levels of Fas in a sample of biological fluid, especially urine, are associated with the presence and grade of bladder cancer. Therefore, urine sFas is an independent predictor of bladder cancer presence and invasiveness in patients with past history of non-muscle invasive bladder cancer, outperforming NMP-22. Using the assay methods of the present invention, Fas can be used in a non-invasive test to detect bladder cancer and evaluate its particular biologic aggressiveness (i.e., depth of invasion and histologic differentiation).

The present invention measures elevated urinary levels of soluble Fas (sFas) to detect and gauge the stage of bladder transitional cell carcinoma. sFas levels were determined in cell lysate and supernatant from two human bladder cancer cell lines (e.g., T24 and TCCSUP), and in voided urine levels of 188 consecutive subjects at risk for TCC recurrence, 31 patients with non-cancerous urologic conditions, and 10 healthy subjects. Barbotage cytology and voided nuclear matrix protein 22 (NMP22) levels were recorded. sFas was analyzed continuously and categorically on the basis of its quintile distribution.

In accordance with the present invention, a kit, a method and apparatus are provided for detecting cancer, precancerous conditions or other cell proliferative disorders that includes a substrate comprising one or more sFas binding agents that binds sFas in a sample and one or more reagents that indicate the amount of sFas present in the sample.

The present invention provides a method of screening for cancer or precancer in a patient by obtaining a biological sample from a patient. The biological sample may be in any form and may include bile, blood, plasma, serum, tissue extract, urine or combinations and mixtures thereof. The biological sample is contacted with a component of a standard assay method that selects for sFas protein. The standard assay method includes an enzyme assay, enzyme-linked immunosorbent assay, immunoassay, radioassay, competitive binding assay and combinations thereof. The standard assay may include other assays known to persons of skill in the art. The amount of sFas protein in the biological sample is quantified by a detection method consistent with the standard assay method used in the contacting step.

Additionally, the present invention also provides a method for measuring sFas levels in a biological sample by coating a solid support with a sFas binding agent and exposing a biological sample to the coated solid support. The sFas in the biological sample binds to the sFas binding agent to produce a detectable product. The method provides for exposing the product to a second agent to bind the sFas bound to the solid support and detecting the amount of the second agent bound to the sFas bound to the solid support. The sFas bound to the solid support is correlated to the amount of the second agent detected to the sFas in the biological sample. The sFas binding agent may be anti-Fas antibodies, e.g., as disclosed in U.S. Pat. No. 6,846,637, which relevant portions are incorporated herein by reference.

The present invention also includes a method for automated detection of a cell proliferative disorder by contacting a sample with an antibody that specifically binds to at least a portion of a sFas protein and detecting specific binding between the antibody and the sFas protein, whereby specific binding corresponds to the quantity of the sFas protein in the sample. The sample may be used in an automated screening system to analyze numerous samples.

In accordance with the present invention, a non-invasive method for facilitating diagnosis of a subject for a cancer of epithelial origin is provided. The method includes obtaining a urine sample from the subject and quantifying the presence of the sFas protein in the urine sample and comparing the quantity of the sFas protein to a standard, wherein the quantity of the sFas protein is indicative of the presence of cancer of epithelial origin. The sFas may be quantified using an immunochemical assay, by a radio-immune assay, by an enzyme-linked immunosorbant assay, an ELISA assay or combination thereof that interact with sFas to produce a detectable signal.

Additionally, the present invention provides a non-invasive kit for facilitating diagnosis of a subject for a cancer. The kit may be used to detect the cancer of epithelial origin is selected from the group consisting of prostate cancer, cancer of the nervous system, breast cancer, retina cancer, lung cancer, skin cancer, kidney cancer, liver cancer, pancreatic cancer, cancer of the genital-urinary or gastrointestinal tract and bladder cancer. The kit is specifically useful in detecting bladder cancer. The kit includes a substrate having a sFas binding agent that binds to the one or more Fas binding agents and one or more reagents that interact with sFas to indicate the amount of sFas present.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term biological sample is a sample that contains cells or cellular material and can be urine, blood, cerebrospinal fluid, pleural fluid, sputum, peritoneal fluid, bladder washings, oral washings, tissue samples, touch preps, or fine-needle aspirates, and can be concentrated prior to use. Urine is a particularly useful biological sample. The type of biological sample that is used depends on the type of cancer to be detected. For example, urine and bladder washings provide useful biological samples for the detection of bladder cancer and to a lesser extent prostate or kidney cancer. Pleural fluid is useful for detecting lung cancer, mesothelioma or metastatic tumors and blood is a useful biological sample for detecting leukemia. The term cancer as used herein refers to bladder cancer, lung cancer, breast cancer, ovarian cancer, prostate cancer, colorectal cancer, renal cancer, and leukemia. As used herein the term subject and patient may be used interchangeably to mean a mammal.

In accordance with the present invention, the term cancer refers to apudoma, choristoma, branchioma, malignant carcinoid syndrome, carcinoid heart disease, Walker, basal cell, basosquamous, Brown-Pearce, ductal, Ehrlich tumor, in situ, Krebs 2, merkel cell, mucinous, non small cell lung, oat cell, papillary, scirrhous, bronchiolar, bronchogenic, squamous cell and transitional cell reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxocarcoma, osteoma, osteosarcoma, Ewing's sarcoma, synovioma, adenofibroma, adenolymphoma, carcinosarcoma, chordoma, mesenchymoma, mesonephroma, myosarcoma, ameloblactoma, cementoma, odontoma, teratoma, throphoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepitholioma, neurofibroma, neuroma, paraganglioma, paraganglioma nonchromaffin, antiokeratoma, angioma sclerosing, angiomatosis, glomangioma, hemanqioendothelioma, hemangioma, hemangiopericytoma, hemangiosarcoma, lymphangioma, lymphangiomyoma, lymphangiosaroma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabomyosarcoma, Kaposi's sarcoma, and mast-cell sarcoma.

The Fas signaling pathway is a primary mediator of apoptosis in various physiologic processes such as tumor cell death mediated by cytotoxic T-cells and natural killer cells and maintenance of immune privileged sites such as the eye, testis, brain, and maternal-fetal interface. The transmembrane receptor Fas (e.g., CD95L or APO-1) is a ubiquitously expressed member of the tumor necrosis factor superfamily. Interaction between Fas and Fas ligand (FasL) induces apoptosis in sensitive cells through activation of the intracellular Fas-associated death domain, the recruitment of caspase-8 and the activation of a cascade of proteases, resulting in proteolysis and degradation of chromosomal DNA (e.g., see Science 267:1449, 1995). Cytotoxic T-cells and natural killer cells, via their expression of the Fas receptor can engage the Fas-FasL interaction and induce apoptosis of cancer cells.[7,8] Dysregulation of Fas-mediated apoptosis is thought to play a role in the development and progression of various tumors. Alternative splicing of Fas mRNA can generate soluble forms of Fas that have a deletion or disruption of the membrane-spanning domain, e.g., see J. Immunol 154:2706, 1995).

Several isoforms of the soluble form of Fas (sFas) were reported to be generated by alternative mRNA splicing. (Cheng J, Science 1994; 263: 1759-62; Cascino I, J Immunol 1995; 154: 2706-13; Papoff G, J Immunol 1996; 156: 4622-30). These sFas isoforms block apoptosis mediated by FasL or anti-Fas agonistic antibody, suggesting that the existence of sFas might protect tumor cells from host antitumor immunity. sFas expression has been reported in the supernatant of various tumor cell lines.[11] Patients with various malignancies (e.g., bladder TCC) show elevated levels of sFas in the tissue and blood.[5, 9, 10, 11] Moreover, higher tissue or/and blood levels of sFAS have been associated with adverse pathologic characteristics and poor clinical outcome in various cancers. In bladder cancer, TCC cells express 20-fold lower levels of membrane bound Fas mRNA and up to 50-fold higher levels of sFas mRNA compared to normal uroepithelial cells, e.g., see Urology 63; 392, 2004; Urology 83:698, 1999) In addition, higher serum levels of sFas were associated with bladder cancer presence and increased risk of bladder cancer disease recurrence in patients with papillary TCC.[10]

The levels of sFas in cell lysate and conditioned media of two established, stable bladder cancer cell lines were examined and the association of urinary levels of Fas with bladder cancer presence and characteristics in a case-control study of 188 consecutive patients with a history of bladder cancer presenting for surveillance cystoscopy were assessed. sFas levels in voided urine from 31 patients with non-malignant urologic conditions and 10 healthy subjects were measured. Finally, the diagnostic performance of sFas was compared with that of urinary nuclear matrix protein 22 (NMP22) and cytology for the detection of bladder TCC.

Materials and methods for the bladder cancer cell lines. The Fas in cell lysate and the conditioned media were measured for two human bladder cancer cell lines (e.g., T24 and TCCSUP) obtained from American Type Culture Collection (Rockville, Md., USA). The cell lines were maintained in T-medium containing about 5% fetal bovine serum. To determine intracelullar sFas levels, cells were switched to serum free medium for 48 hrs and then collected and lysed by freezing and thawing three times in 500 µl phosphate buffered saline. To determine sFas levels in cell culture supernatant, the medium was harvested, dialyzed with water for 48 hours at 4° C., concentrated and finally re-suspended in 500 µl phosphate buffered saline.

One study included: (1) 188 consecutive patients with history of bladder cancer presenting for surveillance cystoscopy; (2) 31 patients with other non-cancerous urologic conditions such as benign prostatic hyperplasia, urinary tract infection, urinary retention, incontinence, urolithiasis, and non-cancer related hematuria; and (3) 10 healthy subjects. A voided urine sample was collected for measurement of sFas prior to cystoscopy in all patients. Urine samples were immediately centrifuged and stored at −80° C. Bladder washing samples were collected during cystoscopy for cytology in a subset of 203 of the original 219 study subjects (e.g., 96 had bladder cancer at cystoscopy and 107 did not). There were 153 (e.g., 67%) males and 76 (e.g., 33%) females. The median age for all study subjects was 71.0 years (e.g., range 21 to 94). Overall, 122 patients (e.g., 53%) had a bladder tumor. The 107 patients without bladder tumor belonged to three different categories: patients with past history of bladder cancer but without tumor evidence at cystoscopy (e.g., n=66), patients with urologic pathology other than bladder malignancy (e.g., n=31), and healthy volunteers (e.g., n=10).

sFas measurements. A quantitative assay enzyme-linked immunosorbent assay (ELISA)(e.g., commercially-available from R&D Systems) was used for measurement of sFas levels. The assay is based on the capture of sFas using a solid-phase adsorbed monoclonal antibody followed by subsequent detection using a labeled second monoclonal antibody to sFas. Every sample was run in duplicate and the mean calculated for data analysis. Intra-assay precision coefficient of variation was 15.8±14.9%.

ELISA is a commonly used technique for the detection of antigens and requires the use of a substrate that produces soluble end products, where specific levels of product are read in a spectrophotometer or luminometer. The assay may be performed using different variations of the ELISA, e.g., direct, indirect, or sandwich method. In a properly optimized assay, the intensity of signal generated is directly proportional to the amount of reactant present. Generally, an analyte-specific antibody (capture antibody) is pre-coated onto a microplate or other substrate. A sample is then added and the immobilized antibody binds any analyte present. An enzyme-linked analyte-specific detection antibody binds to a second epitope on the analyte forming the analyte-antibody complex. Substrate is added and converted by the enzyme, thereby producing a colored product or in some cases light emission that is proportional to the concentration of bound analyte.

For example, microtiter plates are coated with capture antibodies. The amount of capture antibodies used to coat the microtiter plates can vary over a wide range, but it is usually in the concentration range of about 20 ug to about 40 ug per well, in 200 ul of buffer for a typical 96-well plate. The sFas can be derived from any convenient source. One such source is human urine. Next, aliquots of a solution containing an excess of labeled antibodies (e.g., polyclonal or monoclonal antibody) are applied to the plates and incubated for a period of time sufficient to permit substantially complete reaction of the labeled antibodies with the sFas bound to the capture antibodies on the plates. Monoclonal antibodies with the specific reactive are known in the art. As a means of visualizing the amount of sFas that is bound to the plate. In addition, variations of chemiluminescent sandwich ELISAs may be used in conjunction with a luminometer or a highly sensitive colorimetric sandwich ELISAs using an alkaline phosphatase-based color amplification system that is read at a specific wavelength may be used with the present invention.

NMP22 measurements. Measurement of urinary NMP22 level was carried out according to the package insert of the kit (e.g., commercially-available from Matritech Inc., Newton, Mass.). The cut off value for assay positivity recommended by the manufacturer and approved by the FDA was used (e.g., equal to or greater than 10 units per mL).

Pathologic examination and cytology grading. All histologic slides were reviewed without knowledge of clinical data. Bladder tumors were staged according to the 1997 TNM classification and assigned a grade according to the WHO classification. Bladder washings were classified as grade 0 (no atypical cells), grade 1 or 2 (low grade atypia), or grade 3 (high grade atypia). Only high-grade atypia was considered positive.

Statistical Analysis. sFas was apalyzed either as continuous variable or as categorically variable on the basis of its quintile distribution in the case and control subjects combined. Spearman correlation coefficients were used to examine the correlation between continuous variables. The association between categorical data was tested using the Fisher's exact test or the Chi square test. Differences in continuous variables across categorical variables were tested using the Mann-Whitney U test or the Kruskal Wallis test. Non-parametric receiver operating characteristics (ROC) curves in which the value for sensitivity is plotted against false positive rate (1-specificity) were generated. Areas under the curves (AUC) were compared using non-parametric Mann Whitney U-statistics.[8] Univariable and multivariable logistic regression analyses were used to calculate odds ratios and 95% CI. Age, sFas, and NMP22 had skewed distributions and therefore were modeled with a logarithmical transformation for logistic regression analyses. Tumor stage was stratified as Tis and Ta versus T1 and above; tumor grade was stratified by grade 1 and 2 versus grade 3. Statistical significance was set as $p<0.05$ and all reported p values were two-sided. All analyses were performed with SPSS version 11.0 for Windows.

sFas was present in cell lysate and conditioned media from both cell lines. sFas levels were higher in TCC patients (e.g., n=122) than in control subjects (e.g., $p<0.001$). Higher levels of sFas were associated with positive cytology assay results (e.g., $p<0.001$), higher NMP22 levels (e.g., $p<0.001$), NMP22 levels above 10 units/mL (e.g., $p<0.001$), and tumor of stage T1 and greater (e.g., $p<0.001$). The areas under the receiver operating characteristics (ROC) curves of sFas and NMP22 for bladder cancer detection were 0.757 (e.g., 95% CI: 0.694-0.819) and 0.704 (e.g., 95% CI: 0.637-0.772), respectively. In the greater than 75% sensitivity region of the ROC curves, sFas was consistently more specific than NMP22. In multivariate analyses, sFas, NMP22, and cytology were associated with bladder cancer presence (e.g., p-values$\leq$0.009), but only sFas and cytology were associated with less than or equal to T1 tumor stage (e.g., p-values$\leq$0.026).

sFas in Bladder Cancer Cell Lines. sFas was found in cell lysate and supernatant of both TCC SUP and T24 cells. The results for sFas are found in Table 1, briefly, the mean ($\pm$ standard deviation) concentration of sFAS in TCC SUP cells was 189.1±67.9 ng/mL and 77.1±58.2 ng/mL, respectively. The mean ($\pm$ standard deviation) concentration of sFAS in T24 cells was 722.0±25.9 ng/mL and 2279.5±29.1 ng/mL, respectively.

TABLE 1 sFAS IN BLADDER CANCER CELL LINES

| Cell line | Differentiation | sFAS levels (mean ± SD; ng/mL) | |
|---|---|---|---|
| | | Cell lysate | Supernatant |
| RT4 | Grade 1 | 77 ± 58 | 189 ± 68 |
| 5637 | Grade | 345 ± 22 | 291 ± 46 |
| TCC-SUP | Grade 3 | 1734 ± 93 | 476 ± 71 |
| T24 | Grade 3 | 2279 ± 29 | 722 ± 26 | sFas present in both, cell lysate and conditioned media, of established human bladder cancer cell lines.
sFas levels increase with advancing tumor de-differentiation.

Association of Patient Characteristics and Urinary Levels of sFas and NMP22 with Bladder Cancer Presence. Association of urinary sFas, cytology, gender, NMP22, and age with cancer presence is shown in Table 2. sFas and NMP22 levels were both higher in patients with bladder cancer than levels in control subjects when analyzed as continuous or categorical variable (e.g., p values<0.001). The distribution of sFas in bladder cancer cases was skewed towards the highest quintile compared to control subjects. Abnormal urinary cytology was associated with bladder cancer (e.g., $p<0.001$). Patients with bladder cancer were older than those without (e.g., $p<0.001$).

Table 2 is a table of the association of urinary leels of soluable Fas and patient characteristics with transitional cell carcinoma of the urinary bladder.

|  | No. Subjects (%) | Case Subjects (n = 122) | Control Subjects (n = 107) | p |
|---|---|---|---|---|
| Age (median, range) | 229 | 73.1 (40.2-94.2) | 69.9 (21.0-86.3) | <0.001† |
| Urinary creatinine* (median, IQR; mg/dL) | 170 (74) | 66.0 (61.0) | 65.1 (56.9) | 0.691† |
| Gender (No Pts, %) |  |  |  |  |
| Female | 76 (33) | 34 (28) | 42 (39) |  |
| Male | 153 (67) | 88 (72) | 65 (61) | 0.091‡ |
| Urinary cytology* (No Pts, %) |  |  |  |  |
| Positive | 62 (30.5) | 52 (84) | 10 (16) |  |
| Negative | 141 (69.5) | 44 (31) | 97 (69) | <0.001‡ |
| Urinary NMP22 levels |  |  |  |  |
| Continuous (median, IQR; Units/mL) | 229 | 9.9 (54.4) | 2.8 (4.4) | <0.001† |
| Dichotomous (No Pts; %) |  |  |  |  |
| Below 10 Units/mL | 152 (66) | 61 (40) | 91 (60) |  |
| 10 Units/mL and higher | 77 (34) | 61 (79) | 16 (21) | <0.001‡ |
| Urinary sFas levels |  |  |  |  |
| Continuous (median, IQR; ng/mL) | 229 | 129.5 (206.6) | 43.4 (73.2) | <0.001† |
| Quintile Distribution (No Pts; %) |  |  |  |  |
| 1st Quintile | 45 (20) | 11 (24) | 34 (75) |  |
| 2nd Quintile | 46 (20) | 18 (39) | 28 (61) |  |
| 3rd Quintile | 46 (20) | 19 (41) | 27 (59) |  |
| 4th Quintile | 46 (20) | 34 (74) | 12 (26) |  |
| 5th Quintile | 46 (20) | 40 (87) | 6 (13) | <0.001§ |

With sFas = soluble FAS; NMP22 = nuclear matrix protein 22; IQR = interquartile range;
*Urinary Creatinine was unavailable in 39 patients; wash urinary cytology was unavailable in 26 patients;
†Mann-Whitney U test;
‡Fisher's exact test; and
§Chi-square test.

When evaluated in patients with negative barbotage cytology assays (e.g., n=107), continuous sFas levels were higher in patients with bladder cancer than those in control subjects (e.g., median (IQR): 116 ng/mL (175.1) versus 39.9 ng/mL (74.3), respectively; p<0.001). Moreover, 25/44 patients (57%) with bladder cancer and a negative barbotage cytology were found to have high levels of sFas (e.g., quintiles 4 and 5).

Association of Urinary Levels of sFas with Select Patient Characteristics. Association of urinary levels of sFas analyzed as continuous or categorical variable with patient characteristics are shown in Table 3, which is a Distribution of urinary levels of soluble Fas across selected patient characteristics.

Table 3 is a distribution of urinary levels of sFas across selected patient characteristics.

|  | Soluble Fas | | | | | | | |
|---|---|---|---|---|---|---|---|---|
|  | Continuous variable | | | Categorical variable | | | | |
|  | No. Pts (%) | Median levels (IQR) | p‡ | 1st Q (No. Pts, %) | 2nd Q (No. Pts, %) | 3rd Q (No. Pts, %) | 4th Q (No. Pts, %) | 5th Q (No. Pts, %) | p§ |
| Gender |  |  |  |  |  |  |  |  |  |
| Female | 76 (33) | 66.4 (184.2) |  | 26 (17) | 33 (22) | 32 (210) | 32 (21) | 30 (20) |  |
| Male | 153 (67) | 76.0 (144.5) | 0.466 | 19 (25) | 13 (17) | 14 (18) | 14 (18) | 16 (21) | 0.640 |
| Cytology* |  |  |  |  |  |  |  |  |  |
| Positive | 141 | 53.6 (100.2) |  | 38 (27) | 33 (23) | 29 (21) | 27 (19) | 14 (10) |  |
| Negative | 62 | 116.4 (195.9) | <0.001 | 4 (7) | 10 (16) | 12 (19) | 15 (24) | 21 (34) | <0.001 |

-continued

| | Soluble Fas | | | | | | | |
|---|---|---|---|---|---|---|---|---|
| | Continuous variable | | | Categorical variable | | | | |
| | No. Pts (%) | Median levels (IQR) | P‡ | $1^{st}$ Q (No. Pts, %) | $2^{nd}$ Q (No. Pts, %) | $3^{rd}$ Q (No. Pts, %) | $4^{th}$ Q (No. Pts, %) | $5^{th}$ Q (No. Pts, %) | p§ |
| Urinary NMP22 levels | | | | | | | | |
| Below 10 Units/mL | 152 (66) | 55.1 (94.4) | | 39 (26) | 36 (24) | 34 (22) | 30 (20) | 13 (9) | |
| 10 Units/mL and higher Pathologic Stage† | 77 (34) | 167.8 (344.5) | <0.001 | 6 (8) | 10 (13) | 12 (16) | 16 (21) | 33 (43) | <0.001 |
| Tis or Ta | 72 | 98.0 (132.0) | | 8 (11) | 14 (19) | 14 (19) | 23 (32) | 13 (18) | |
| T1 or higher stage Pathologic Grade† | 50 | 250.0 (476.9) | <0.001 | 3 (6) | 4 (8) | 5 (10) | 11 (22) | 27 (54) | <0.001 |
| 1 or 2 | 85 | 109.0 (155.2) | | 8 (9) | 12 (14) | 15 (18) | 27 (32) | 23 (27) | |
| 3 | 37 | 171.8 (425.7) | 0.074 | 3 (8) | 6 (16) | 4 (11) | 7 (19) | 17 (46) | 0.264 |

Where IQR = interquartile range;
*Wash urinary cytology was unavailable in 26 patients;
†Pathologic stage and grade were available in the 122 patients who underwent surgery for bladder cancer;
‡Fisher's exact test; and
§Mann-Whitney U test.

Patients with positive urinary cytology assay results or NMP22 levels equal to or above 10 Units/ML had significantly higher sFas levels than those with negative assay results or NMP22 levels below 10 Units/mL, respectively. Bladder cancer patients with invasive tumor stage (e.g., T1 and higher stage) had significantly higher sFas levels than those with Tis or Ta tumor stage. Continuous urinary sFas levels were correlated with continuous NMP22 levels (e.g., r=0.414, p<0.001) and patient age at time of specimen collection (e.g., r=0.264, p<0.001). Patient age increased incrementally with increasing sFas quintiles (e.g., p=0.003).

Figure 1:
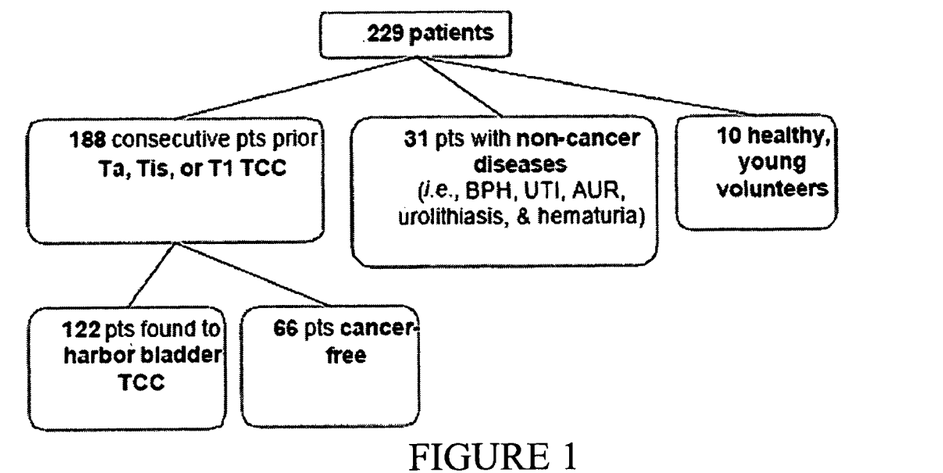
FIG. 1 is a chart that outlines the patient population.
Figure 2:
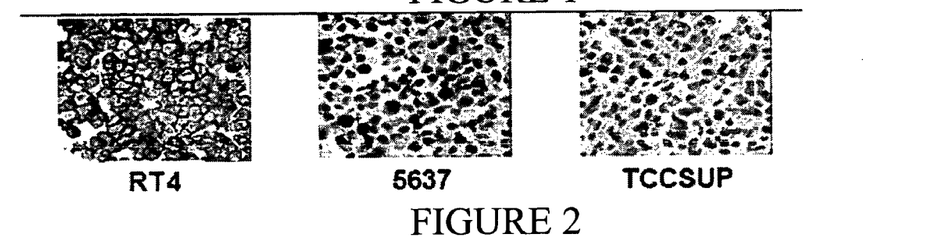
FIG. 2 shows the FAS IHC staining of bladder TCC cell lines.
Figure 3:
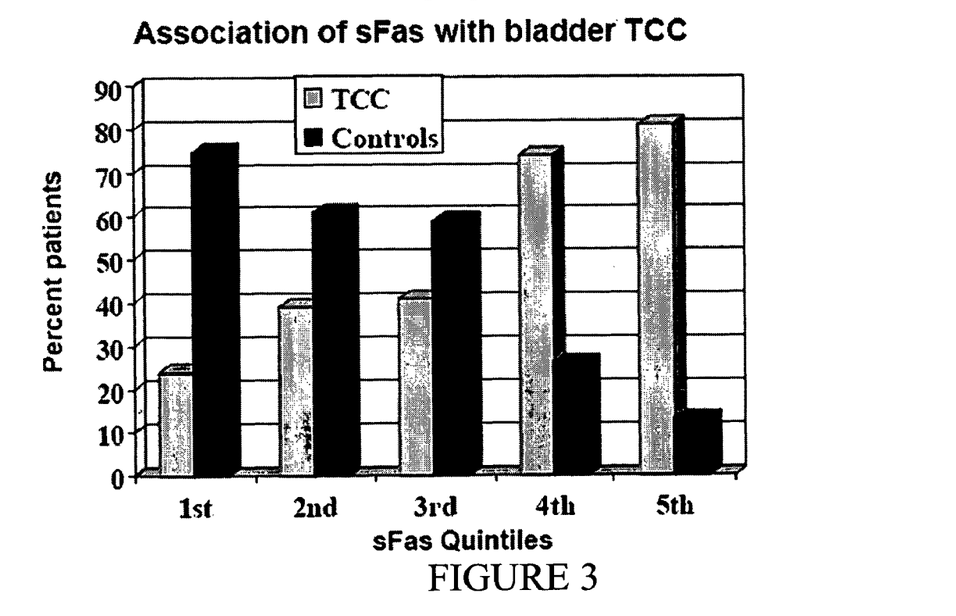
FIG. 3 is a graph that shows the association of sFas with bladder TCC.
Figure 4:
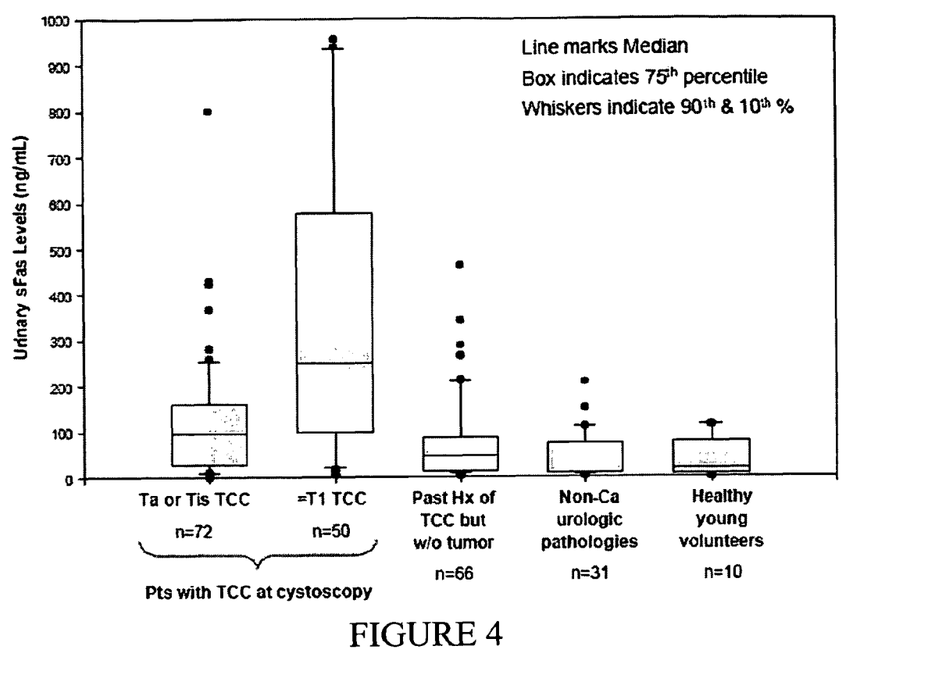
FIG. 4 is a graph that shows the levels of sFas from various tissue and cell samples.
Figure 5:
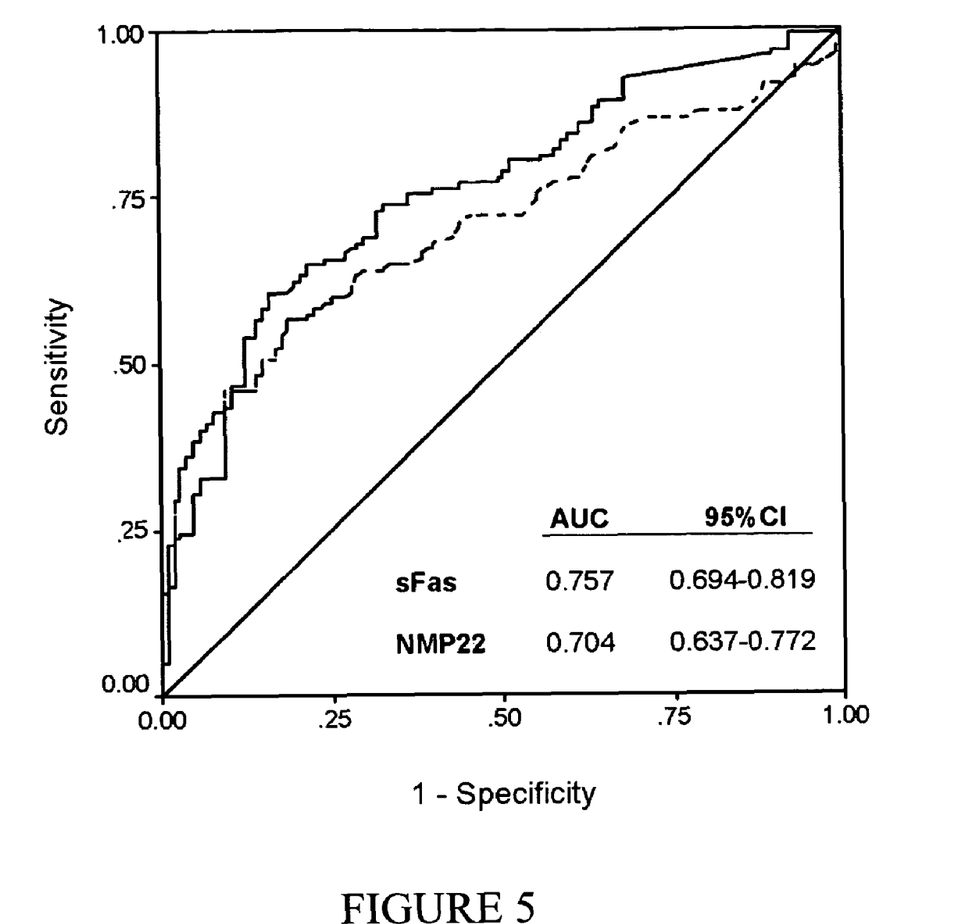
FIG. 5 is a plot of the sensitivity verses the specificity for NMP22 and sFas of the present invention.

Diagnostic Performance of Urinary sFas for Prediction of Bladder Cancer Presence and Stage. The ability of urinary levels of sFas and NMP22 to predict cystoscopic findings was analyzed using non-parametric ROC analyses. When analyzed in all patients, NMP22 and sFas were both more accurate than guessing (e.g., null hypothesis; area under the null hypothesis=0.5) for predicting bladder cancer presence (e.g., p values<0.001). With reference to FIG. 5, a graph of the sensitivity verses specificity for NMP22 and sFas, the overall AUCs for sFas and NMP22 were not statistically different from each other (e.g., p=0.872). In the high sensitivity region of the ROC curves (e.g., sensitivity greater than about 75%), sFas was consistently more specific than NMP22 yielding a larger partial AUC than NMP22. In patients with negative cytology, sFas was more accurate than guessing for predicting bladder cancer presence (e.g., AUC: 0.715, 95% CI: 0.622-0.809; p<0.001), whereas NMP22 was not (e.g., AUC: 0.603, 95% CI: 0.491-0.715; p=0.051).

In a multivariable logistic regression analysis seen in Table 4, higher sFas and NMP22 and positive cytology assay result were all three associated with an increased risk of bladder cancer presence after adjusting for the effect of patient age. Higher sFas and positive cytology assay result were both associated with invasive tumor stage after adjusting for the effects of patient age and NMP22. sFas retained its association with bladder cancer presence and stage when analyzed as categorical variable in multivariate analyses that adjusted for the effects of cvtology, NMP22, and patient age (e.g., p values less than 0.001).

| | Odds ratio | 95% CI | p |
|---|---|---|---|
| Prediction of Bladder Cancer | | | |
| | 1.028 | 0.997-1.060 | 0.078 |
| Nuclear matrix protein 22† | 2.863 | 1.305-6.280 | 0.009 |
| | 7.019 | 3.095-15.917 | <0.001 |
| Soluble Fas* | 3.072 | 1.606-5.876 | 0.001 |
| Prediction of Invasive Tumor Stage (≧T1) | | | |
| Age* | 1.024 | 0.979-1.070 | 0.302 |
| Nuclear matrix protein 22† | 2.158 | 0.777-5.989 | 0.140 |
| Cytology | 3.297 | 1.153-9.426 | 0.026 |
| Soluble Fas* | 3.691 | 1.275-10.686 | 0.016 |

Where
*Age and sFas had a skewed distribution and therefore were modeled with a logarithmical transformation;
†Nuclear matrix protein 22 was analyzed as dichotomous variable (equal to or greater than 10 units per mL).

sFas was present in the cell lysate and conditioned media of two established human bladder cancer cell lines. Higher urinary levels of sFas were associated with positive cytology assay results, higher urine levels of NMP22 evaluated either as categorical or continuous variable, and invasive tumor stage. After controlling for the effects of cvtology, NMP22, and patient age, higher sFas was an independent predictor of bladder cancer presence and invasiveness. This association remained significant in patients with a normal cytology assay result. While the overall performances for the detection of bladder cancer of urine sFas and NMP22 were not significantly different from each other, at the clinically relevant range for a detection marker (e.g., sensitivity values above 75%), sFas had consistently a higher specificity than NMP22.

The higher urine levels of sFas were associated with bladder cancer presence, characteristics, and biologic aggressiveness. The Fas-FasL system plays an important role in the killing mechanisms of natural killer cells and cytotoxic T-cells. Thus, blocking of the signaling pathway through Fas-FasL is one mechanism of the tumor cell's escape from host immune surveillance. An important inhibitor for this pathway is sFas, which is produced by an alternative splicing and lacks the transmembrane domain of the native Fas cDNA fragment. sFas has been shown to antagonize both anti-Fas mAb- and FasL-mediated tumor cell lysis through competition for the binding of surface Fas to FasL. The presence of urinary sFas was an independent predictor of bladder TCC presence and invasiveness (e.g., stage≧T1) after adjusting for the effects of pre-cystoscopic variables (i.e., age, cytology, and NMP-22 levels). The strong association of sFas with bladder cancer presence and aggressiveness remained true in patients with negative barbotage cytology assay results. For example, fifty seven percent of patients with bladder cancer but with negative cytology assay result had high sFas levels (e.g., the $4^{th}$ and $5^{th}$ quintiles). This together with the independent value for predicting bladder cancer presence and biological aggressiveness suggest that urinary sFas complements cytology and improves current diagnostic protocols.

Urine levels of sFas were superior to those of NMP22 for both bladder cancer detection and staging. NMP22 is one of only two markers approved by the FDA both for initial diagnosis of bladder cancer in patients with hematuria and for monitoring for disease recurrence in patients previously diagnosed with bladder cancer. Though not statistically significantly different, sFas had a 5.1% higher overall AUC for detecting bladder cancer than NMP22. Furthermore, urine sFas had a higher diagnostic accuracy than urine NMP22 for the detection of bladder cancer in the portion of the ROC curve that is relevant in clinical practice (e.g., ≧75% sensitivity). Moreover, in patients with negative cytology, sFas was associated with bladder cancer presence, whereas NMP22 was not. Finally, sFAS was independently associated with invasive bladder cancer at diagnosis. Predicting advanced pathologic stage is important since it may help reduce mortality and morbidity of the disease by allowing timely, tailored treatment. The superior specificity of sFas over NMP22 for bladder cancer at clinically relevant sensitivities together with sFas's independent association with the risk of bladder cancer support the hypothesis that sFas can improve the diagnostic accuracy of NMP22 and urine cytology for distinguishing between bladder cancer and benign cases.

Varying sources of sFas production can contribute to the level found in urine of patients with bladder TCC. The differential contribution from blood levels filtered through the kidney and direct release from cells in the urinary epithelium remains to be elucidated. The glomerular capillary wall functions as a filter that allows the passage of small molecules but almost completely restricts the passage of large molecules such as albumin (e.g., 66 kD). In addition to size, the shape and charge of the molecule are important determinants in a molecules' glomerular permeability. sFas has an estimated weight of 48-52 kD but, its glomerular permeability has not been evaluated. Indirect evidence, however, suggests that serum sFas is at least partially filtered by the kidney. Elevated serum levels of sFas are seen in patients with renal failure compared to controls due to a decreased urinary sFas excretion secondary to poor glomerular filtration.

To analyze the source of sFas in bladder cancer, the expression sFas in two established high-grade TCC cell lines (e.g., T24 and TCCSUP) were examined. Various studies have shown sFas to be present in the supernatant of different tumor cell lines.[11] Perabo and colleagues detected sFas in cell culture supernatants of both low and high grade bladder cancer cell lines using an ELISA assay. Other authors reported that bladder TCC cell lines express up to 50-fold higher levels of sFas mRNA compared to primary normal uroepithelial cells (Urology 63; 392, 2004; 83:698, 1999). Substantial sFas levels in cell culture lysate and supernatant by ELISA from both bladder cancer cell lines were detected, suggesting that TCC cells could have the ability to produce sFas in vitro and in vivo. The expression of sFas can be enhanced by various serine proteases such as urokinase-type plasminogen activator (uPA). Additionally, urine and plasma levels of both uPA and it's receptor, were elevated in patients with bladder TCC when compared to healthy controls (J. Urol 2003 170: 2244-7; Urology 61: 1053-8; 2003). In addition, pre-operative plasma uPA is an independent predictor of lymphovascular invasion, metastases to regional lymph nodes, disease progression and death from bladder cancer in patients who have undergone cystectomy (Urology 61: 1053-8, 2003).

Bladder TCC cells produce and secrete sFas as it is present in the cell lysate and supernatant of established bladder cancer cell lines, In vitro. In vivo, urine sFas was found to be an independent predictor of bladder cancer presence and invasiveness in patients with a history of bladder cancer. The present invention uses urinary sFas for both bladder cancer detection and staging and outperforms urinary NMP22.

TABLE 5

Urine sFas is superior to NMP22.

| | All patients (n = 229) | | | Patients with negative cytology (n = 141) | | |
|---|---|---|---|---|---|---|
| | AUC | 95% CI | P value | AUC | 95% CI | P value |
| sFas | 0.757 | 0.694-0.819 | <0.001 | 0.715 | 0.622-0.809 | <0.001 |
| NMP22 | 0.704 | 0.637-0.772 | <0.001 | 0.603 | 0.491-0.715 | 0.051 |

Urine sFas superior to NMP22:
Higher AUC for the detection of bladder cancer when evaluated in all patients and in patients with negative cytology
sFas had a consistently a higher specificity than NMP22 at sensitivity values above 75%

| | Odds ratio | 95% CI | p |
|---|---|---|---|
| | Bladder Cancer Presence | | |
| Age | 1.028 | 0.997-1.060 | 0.078 |
| NMP22† | 2.863 | 1.305-6.280 | 0.009 |
| Cytology | 7.019 | 3.095-15.917 | <0.001 |
| sFas | 3.072 | 1.606-5.876 | 0.001 |
| | Invasive Tumor Stage (=T1) | | |
| Age | 1.024 | 0.979-1.070 | 0.302 |
| NMP22† | 2.158 | 0.777-5.989 | 0.140 |
| Cytology | 3.297 | 1.153-9.426 | 0.026 |
| sFas | 3.691 | 1.275-10.686 | 0.016 |

†Nuclear matrix protein 22 was analyzed as dichotomous variable (equal to or greater than 10 units per mL).
Higher sFas independently associated with bladder cancer recurrence and progression to invasive tumor stage (>T1).

In accordance with the present invention, a method, kit and device are provided that allow for detecting cancer of genitorurinary tract including a substrate having one or more sFas binding agents, wherein sFas in a sample binds to the one or more sFas binding agents and one or more reagents that indicate the amount of sFas present in the sample.

The present invention provides a method of screening for cancer or precancer in a patient by obtaining a biological sample from a patient. The biological sample may be in any form and may include bile, blood, plasma, serum, tissue extract, urine or combinations and mixtures thereof. The biological sample is contacted with a component of a standard assay method that selects for sFas protein. The standard assay method includes an enzyme assay, enzyme-linked immunosorbent assay, immunoassay, radioassay, competitive binding assay and combinations thereof. The standard assay may include other assays known to persons of skill in the art. The amount of sFas protein in the biological sample is quantified by a detection method consistent with the standard assay method used in the contacting step.

In some instances, the subject may have been treated for cancer, precancer or other cell proliferative disorder either surgically, hormonally or combinations thereof. Additionally, the biological sample may be obtained from a patient currently or previously treated for cancer, precancer or other cell proliferative disorder.

The biological sample used may be urine, blood, cerebrospinal fluid, pleural fluid, sputum, peritoneal fluid, bladder washings, oral washings, tissue samples, touch preps, or fine-needle aspirates, and can be concentrated prior to use. Urine is a particularly useful biological sample. The method of the present invention is useful for detecting cancers such as bladder cancer, lung cancer, breast cancer, ovarian cancer, prostate cancer, colorectal cancer, renal cancer, and leukemia. The method is particularly suited for detecting bladder cancer.

Additionally, the cancer may be a neoplasm of the bone, digestive system, liver, pancreatic, pituitary, testicular, orbital, head and neck, central nervous system, acoustic, genitor-urinary tract, pelvic, respiratory tract, urogenital neoplasm, neurofibromatosis, and cervical dysplasia. Specifically, the method may be used to detect cancer of genitor-urinary tract, and more specifically bladder cancer.

The standard assay method uses a detectable label capable of generating a measurable signal. The detectable label may be in the form of a compound that absorbs energy, emits energy, or converts energy into a signal. In some instances, the label forms a colored sample that may be quantified using absorbance or florescence. In addition, the sample may produce a value relating to the quantity of sFas in the sample or may indicate the presence or absence, e.g., (+) or (−).

The amount of sFas in a sample may be compared to a specific standard value indicative of the presence of a biological condition. Instead of a specific standard value the standard value may be a curve, plot or range that is indicative of the likelihood of the existence of a biological condition.

The component of a standard assay method that selects for sFas protein may be attached or linked to a solid support. In some instances, the solid support may be a microtiter plate but in other instances, the solid support may be a diagnostic device for individual use or automated processing. A sFas specific antibody may be attached to the support to bind sFas. However, the skilled artisan will know that other binding agents may be used, e.g., proteins, DNA, RNA, polymers, nitrocellulose, nylon, etc. In some instances, a nonspecific binding agent may be used to bind the sFas in a sample. The bound sFas may then interact with a second agent to produce a detectable signal. The second agent may be a specific antibody, that binds sFas and produce a detectable signal. The detection may also be linked to a protein or enzyme that in-turn is processed to produce a detectable signal.

The present invention also provides a method for measuring sFas levels in a biological sample by coating a solid support with a sFas binding agent and exposing a biological sample to the coated solid support. The sFas in the biological sample binds to the sFas binding agent to produce a detectable product. The method provides for exposing the product to a second agent to bind the sFas bound to the solid support and detecting the level of the second agent bound to the sFas bound to the solid support. The sFas bound to the solid support is correlated to the amount of the second agent detected to the sFas in the biological sample.

The sFas bound to the solid support may be detected by an enzyme assay, an enzyme-linked immunosorbent assay, an immunoassay, a radioassay, a competitive binding assay and combinations thereof. The detection may be made using a detectable label capable of generating a measurable signal. The detectable label may be in the form of a compound that absorbs energy, emits energy or converts energy into a signal. In some instances, the label forms a colored sample that may quantified using absorbance or florescence. In addition, the sample may produce a value relating to the quantity of sFas in the sample or may indicate the presence or absence, e.g., + or −.

The sFas binding agent that selects for sFas protein may be attached or linked to a solid support. In some instances, the solid support may be a microtiter plate but in other instances, the solid support may be a diagnostic device for individual use or automated processing. A sFas specific antibody may be attached to the support to bind sFas; however, the skilled artisan will know that other binding agents may be used, e.g., proteins, DNA, RNA, polymers, nitrocellulose, nylon, etc. In some instances, a nonspecific binding agent may be used to bind the sFas in a sample. The bound sFas may then interact with a second agent to produce a detectable signal. The second agent may be a specific antibody, that binds sFas and produce a detectable signal. The detection may also be linked to a protein or enzyme that in-turn is processed to produce a detectable signal.

The present invention includes a method for automated detection of a cell proliferative disorder by contacting a sample with an antibody that specifically binds to at least a portion of a sFas protein and detecting specific binding between the antibody and the sFas protein, whereby specific binding corresponds to the quantity of the sFas protein in the sample. The sample may be used in an automated screening system to analyze numerous samples.

The present invention also includes a non-invasive method for facilitating diagnosis of a subject for a cancer of epithelial origin by obtaining a urine sample from the subject and quantifying the presence of the sFas protein in the urine sample and comparing the quantity of the sFas protein to a standard, wherein the quantity of the sFas protein is indicative of the presence of cancer of epithelial origin. The sFas may be quantified using an immunochemical assay, by a radio-immune assay, by an enzyme-linked immunosorbant assay, an ELISA assay or combination thereof that interact with sFas to produce a detectable signal.

Additionally, the present invention provides a non-invasive kit for facilitating diagnosis of a subject for a cancer. The kit may be used to detect the cancer of epithelial origin is selected from the group consisting of prostate cancer, cancer of the nervous system, breast cancer, retina cancer, lung cancer, skin cancer, kidney cancer, liver cancer, pancreatic cancer, cancer of the genital-urinary or gastrointestinal tract and bladder cancer. The kit is specifically useful in detecting bladder cancer. The kit may be used as a home detection kit, a clinical kit or a commercial kit.

The kit includes a substrate having a sFas binding agent that binds to the one or more Fas binding agents and one or more reagents that interact with sFas to indicate the amount of sFas present. The sFas binding agent may be attached or linked to a solid support. In some instances, the solid support may be a microtiter plate but in other instances, the solid support may be a diagnostic device for individual use or automated processing. A sFas specific antibody may be attached to the support to bind sFas; however, the skilled artisan will know that other binding agents may be used, e.g., proteins, DNA, RNA, polymers, nitrocellulose, nylon, etc. In some instances, a nonspecific binding agent may be used to bind the sFas in a sample. The bound sFas may then interact with a second agent to produce a detectable signal. The second agent may be a specific antibody, that binds sFas and produce a detectable signal. The detection may also be linked to a protein or enzyme that in-turn is processed to produce a detectable signal.

The sFas bound to the solid support may be detected by an enzyme assay, an enzyme-linked immunosorbent assay, an immunoassay, a radioassay, a competitive binding assay and combinations thereof. The detection may be made using a detectable label capable of generating a measurable signal. The detectable label may be in the form of a compound that absorbs energy, emits energy or converts energy into a signal. In some instances, the label forms a colored sample that may quantified using absorbance or florescence. In addition, the sample may produce a value relating to the quantity of sFas in the sample or may indicate the presence or absence, e.g., + or −.

Using the present invention it was found that, in vitro, sFas was present in the cell lysate and supernatant of high-grade bladder cancer cell lines suggesting that it is likely to be produced and released by bladder TCC cells. It was also found that in patients with history of non-invasive bladder cancer, urinary sFAS• is a strong, independent predictor of bladder cancer recurrence and biologic aggressiveness in all patients and in patients with negative barbotage cytology is superior to NMP22 for both bladder cancer detection and staging. Using the present invention it is possible to: (1) find that levels of sFAS are higher overall AUC for detection of bladder cancer; (2) sFAs higher diagnostic accuracy for the detection of bladder cancer in the portion of the ROC curve with sensitivity=75%; (c) sFas independently associated with invasive bladder cancer at diagnosis, whereas NMP22 was not; and (4) sFAS associated with bladder cancer presence in patients with negative cytology, whereas NMP22 was not. Therefore, urinary sFas serves as novel voided urine biomarker for bladder cancer surveillance. Elevated levels of urinary levels of sFas in patients with bladder TCC lead to a more effective clinical management as well as provide new targets for therapy in these patients.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Rubben, H., Lutzeyer, W., Fischer, N. et al.: Natural history and treatment of low and high risk superficial bladder tumors. J Urol, 139: 283, 1988.
2. Millan-Rodriguez, F., Chechile-Toniolo, G., Salvador-Bayarri, J. et al.: Primary superficial bladder cancer risk groups according to progression, mortality and recurrence. J Urol, 164: 680, 2000.
3. Heney, N. M.: Natural history of superficial bladder cancer. Prognostic features and long-term disease course. Urol Clin North Am, 19: 429, 1992.
4. Heney, N. M., Ahmed, S., Flanagan, M. J. et al.: Superficial bladder cancer: progression and recurrence. J Urol, 130: 1083, 1983.

5. Mizutani, Y., Yoshida, O., Bonavida, B.: Prognostic significance of soluble Fas in the serum of patients with bladder cancer. J Urol, 160: 571, 1998.
6. Nagata, S.: Fas and Fas ligand: a death factor and its receptor. Adv Immunol, 57: 129, 1994.
7. Kagi, D., Vignaux, F., Ledermann, B. et al.: Fas and perforin pathways as major mechanisms of T cell-mediated cytotoxicity. Science, 265: 528, 1994.
8. Arase, H., Arase, N., Saito, T.: Fas-mediated cytotoxicity by freshly isolated natural killer cells. J Exp Med, 181: 1235, 1995.
9. Mizutani, Y., Hongo, F., Sato, N. et al.: Significance of serum soluble Fas ligand in patients with bladder carcinoma. Cancer, 92: 287, 2001.
10. Mizutani, Y., Yoshida, O., Ukimura, O. et al.: Prognostic significance of a combination of soluble Fas and soluble Fas ligand in the serum of patients with Ta bladder cancer. Cancer Biother Radiopharm, 17: 563, 2002.
11. Perabo, F. G., Mattes, R. H., Wirger, A. et al.: Soluble Fas and Fas-ligand in bladder cancer in vitro and in vivo. Urol Oncol, 6: 163, 2001.
12. DeLong, E. R., DeLong, D. M., Clarke-Pearson, D. L.: Comparing the areas under two or more correlated receiver operating characteristic curves: a nonparametric approach. Biometrics, 44: 837, 1988.
13. Pawelec, G.: Immunotherapy and immunoselection—tumour escape as the final hurdle. FEBS Lett, 567: 63, 2004.
14. O'Connell, J., Houston, A., Bennett, M. W. et al.: Immune privilege or inflammation? Insights into the Fas ligand enigma. Nat Med, 7: 271, 2001.
15. Lee, S. H., Lee, J. Y., Park, W. S. et al.: Transitional cell carcinoma expresses high levels of Fas ligand in vivo. BJU Int, 83: 698, 1999.
16. Chopin, D., Barei-Moniri, R., Maille, P. et al.: Human urinary bladder transitional cell carcinomas acquire the functional Fas ligand during tumor progression. Am J Pathol, 162:1139, 2003.
17. Liu, C., Cheng, J., Mountz, J. D.: Differential expression of human Fas mRNA species upon peripheral blood mononuclear cell activation. Biochem J, 310 (Pt 3): 957, 1995.
18. Lotan, Y., Roehrborn, C. G.: Sensitivity and specificity of commonly available bladder tumor markers versus cytology: results of a comprehensive literature review and meta-analyses. Urology, 61: 109, 2003.
19. Glas, A. S., Roos, D., Deutekom, M. et al.: Tumor markers in the diagnosis of primary bladder cancer. A systematic review. J Urol, 169: 1975, 2003.

What is claimed is:

1. A method of screening for bladder cancer in a patient comprising the steps of:
   contacting a urine sample from the patient with a component of a standard assay method that detects an sFas protein, wherein the standard assay method comprises an enzyme assay, enzyme-linked immunosorbent assay; immunoassay, radioassay, competitive binding assay and combinations thereof; and
   quantifying the amount of the sFas protein in the urine sample, wherein the presence of sFas is indicative of bladder cancer cells.

2. The method of claim 1, wherein the patient is currently or previously treated for bladder cancer.

3. The method of claim 1, wherein the standard assay method uses a detectable label capable of generating a measurable signal.

4. A non-invasive method for facilitating diagnosis of a subject for a bladder cancer, comprising:
   obtaining a urine sample from the subject;
   quantifying the presence of an sFas protein in the urine sample; and
   comparing the quantity of the sFas protein to a standard, wherein the quantity of the sFas protein is indicative of the presence of bladder cancer.

5. The method of claim 4, wherein subject has previously been treated surgically or hormonally.

6. The method of claim 4, wherein the sFas is quantified by an immunochemical assay, by a radio-immune assay, by an enzyme-linked immunosorbant assay, an ELISA assay or combination thereof.

7. A method of screening for intermediate-grade or high-grade bladder cancer in a patient, said method comprising the steps of:
   obtaining a urine sample from the subject;
   quantifying the presence of an sFas protein in the urine sample; and
   comparing the quantity of the sFas protein to a standard, wherein the quantity of the sFas protein is indicative of the presence of bladder cancer.

8. A method for detecting a recurrence of bladder cancer in a subject, the method comprising the steps of:
   obtaining a urine sample from the subject;
   quantifying the presence of an sFas protein in the urine sample; and
   comparing the quantity of the sFas protein to a standard, wherein the quantity of the sFas protein is indicative of the presence of bladder cancer.

9. A method for detecting bladder cancer in a subject, the method comprising the steps of:
   obtaining a urine sample from the subject; and
   detecting an sFas protein in the urine sample, wherein an increase in the level sFas protein in urine when compared to normal subjects is indicative of a bladder cancer of intermediate grade or greater.

10. The method of claim 9, wherein the patient is currently or previously treated for bladder cancer.

11. The method of claim 9, wherein the standard assay method uses a detectable label capable of generating a measurable signal.

12. The method of claim 9, wherein subject has previously been treated surgically or hormonally.

13. The method of claim 9, wherein the sFas is quantified by an immunochemical assay, by a radio-immune assay, by an enzyme-linked immunosorbant assay, an ELISA assay or combination thereof.

14. The method of claim 9, wherein a significant increase in sFas in urine is indicative of bladder cancer that is grade Tis, Ta or greater.

15. The method of claim 9, wherein an increase in a previously detected level of the sFas in urine from a patient with grade Tis or Ta bladder cancer is indicative of bladder cancer that has progressed to grade T1 or greater.

16. The method of claim 9, wherein an increase in the level of the sFas detected in urine from when the bladder cancer was level Tis or Ta is indicative of bladder cancer that is invasive.

* * * * *